United States Patent [19]

Coates et al.

[11] 4,111,935

[45] Sep. 5, 1978

[54] 3-CHLORO-6-PHENYLPYRIDAZINE COMPOUNDS

[75] Inventors: William John Coates, Welwyn Garden City; Anthony Maitland Roe, Hatfield; Robert Antony Slater, Letchworth; Edwin Michael Taylor, Welwyn, all of England

[73] Assignee: Smith Kline & French Laboratories Limited, Welwyn Garden City, England

[21] Appl. No.: 816,993

[22] Filed: Jul. 19, 1977

Related U.S. Application Data

[63] Continuation-in-part of Ser. No. 583,379, Jun. 3, 1975, Pat. No. 4,053,601.

[30] Foreign Application Priority Data

Jan. 2, 1975 [GB] United Kingdom .................... 20/75

[51] Int. Cl.$^2$ ............................................ C07D 237/12

[52] U.S. Cl. .................................. 544/224; 260/343.6; 562/463

[58] Field of Search .................................... 260/250 A

[56] References Cited

U.S. PATENT DOCUMENTS

| 3,558,641 | 1/1971 | Sarett et al. ...................... 260/250 A |
| 3,687,971 | 8/1972 | Shen et al. ....................... 260/250 A |
| 3,717,659 | 2/1973 | Sarett et al. ...................... 260/250 A |

OTHER PUBLICATIONS

Coates et al., Chem. Abs. 84, 164819j (1976).

*Primary Examiner*—Donald G. Daus
*Assistant Examiner*—Mark L. Berch
*Attorney, Agent, or Firm*—Joan S. Keps; Richard D. Foggio; William H. Edgerton

[57] ABSTRACT

Substituted derivatives of 3-chloro-6-phenylpyridazine which are useful intermediates in the preparation of substituted phenylhydrazinopyridazines which have β-adrenergic blocking and vasodilator activity.

11 Claims, No Drawings

3-CHLORO-6-PHENYLPYRIDAZINE COMPOUNDS

This application is a continuation-in-part of Ser. No. 583,379 filed June 3, 1975, now U.S. Pat. No. 4,053,601.

This invention relates to certain substituted derivatives of 3-chloro-6-phenylpyridazine which are useful intermediates in the preparation of certain substituted phenyl hydrazinopyridazines which have β-adrenergic blocking and vasodilator activity.

The compounds of the present invention are represented by the following Formula 1:

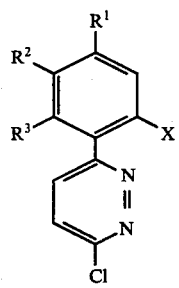

FORMULA 1 wherein two of the groups $R^1$, $R^2$ and $R^3$ are hydrogen and the third group is hydrogen, fluoro, chloro, bromo, hydroxy, lower alkoxy, lower alkenyloxy or lower alkoxycarbonyl; and X is

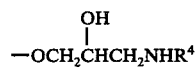

where $R^4$ is isopropyl, tertiary butyl or phenylethyl, or when $R^1$, $R^2$ and $R^3$ are other than hydroxy, X may also be hydroxy.

Throughout the specification and claims, by the terms 'lower alkoxy' and 'lower alkenyloxy' we mean alkoxy and alkenyloxy groups containing a chain of no more than four carbon atoms, which chain may, where possible, be branched.

In a preferred group $R^1$, $R^2$ and $R^3$ are all hydrogen, or one of $R^1$, $R^2$ and $R^3$ is fluoro, chloro or methoxy. Particularly preferably $R^3$ is hydrogen.

Preferably $R^4$ is isopropyl or tertiary butyl. Particularly, R', $R^2$ and $R^3$ are all hydrogen and $R^4$ is isopropyl or tertiary butyl. Examples of particularly preferred compounds which fall within the scope of the present invention are:

3-Chloro-6-(2-hydroxyphenyl)pyridazine
3-Chloro-6-(2-(3-t-butylamino-2-hydroxypropoxy)phenyl pyridazine
3-Chloro-6-(2-(2-hydroxy-3-isopropylaminopropoxy)-phenylpyridazine
3-Chloro-6-(2-hydroxy-4-methoxyphenyl)pyridazine
3-Chloro-6-[2-(3-t-butylamino-2-hydroxypropoxy)-4-methoxyphenyl]pyridazine.

The compounds of this invention wherein X is

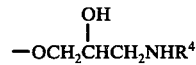

exist as optical isomers; Racemic mixtures can be resolved by conventional methods, such as recrystallisation of salts formed with optically active acids. The S-absolute configuration is preferred.

The compounds of Formula 1 wherein X is OH (represented as Formula 5) may be prepared by the processes outlined in Scheme 1. In the schemes $R^1$, $R^2$ and $R^3$ have the same significance as in Formula 1 or they may also be protected derivatives thereof or precursors thereof.

Scheme 1

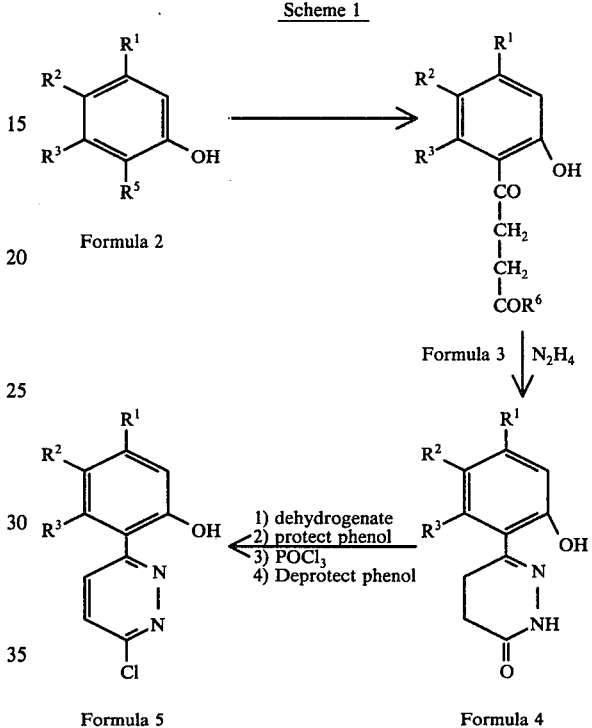

A phenol of Formula 2 (wherein $R^5$ is hydrogen, bromine or —COCH$_3$) is first converted into a compound of Formula 3 (wherein $R^6$ is hydroxy, amino or any other suitable group such as lower alkoxy or lower alkylamino, which can be displaced with hydrazine). When $R^5$ is hydrogen, reaction with succinic anhydride and a Lewis acid such as aluminium trichloride may be used. When $R^5$ is bromine, formation of a Grignard reagent with magnesium, and treatment with, for example, N-methylsuccinimide provides a useful method, the phenol group being protected during this reaction, for example by benzylation. When $R^5$ is —COCH$_3$, the phenol of Formula 2 may be treated with formaldehyde and a di(lower alkyl)amine to give a compound of Formula 6 wherein $R^7$ is lower alkyl or $(R^7)_2$ is a polymethylene chain which forms a heterocyclic ring with the nitrogen atom shown.

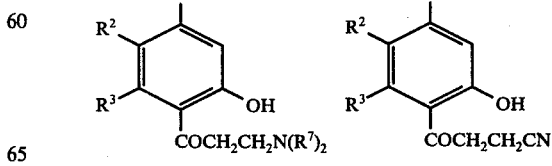

Formula 6    Formula 7

The compounds of Formula 6 may be alkylated to give the corresponding quaternary derivatives. The compounds of Formula 6 and the corresponding quaternary derivatives may be treated with an inorganic cyanide to give a nitrile of Formula 7. The phenol group may be protected, for example as the acetate ester, during these processes. The nitriles of Formula 7 may be hydrolysed to the corresponding amides or carboxylic acids (Formula 3 $R^6 = NH_2$ or OH).

The dihydropyridazinones of Formula 4 may be prepared from the corresponding compounds of Formula 3 by treatment with hydrazine. The chloropyridazines of Formula 5 may be prepared by successive dehydrogenation of a dihydropyridazinone of Formula 4, e.g. by treatment with bromine in acetic acid, sodium 3-nitrobenzenesulphonate or chloranil, followed by protection of the phenolic group, treatment with phosphoryl chloride, and removal of the phenol-protecting group. Suitable phenol-protecting groups are the ethoxycarbonyl (or acetoxy) groups.

An alternative process for the preparation of compounds of Formula 1 wherein X is OH (represented as Formula 5) is outlined in Scheme 2:

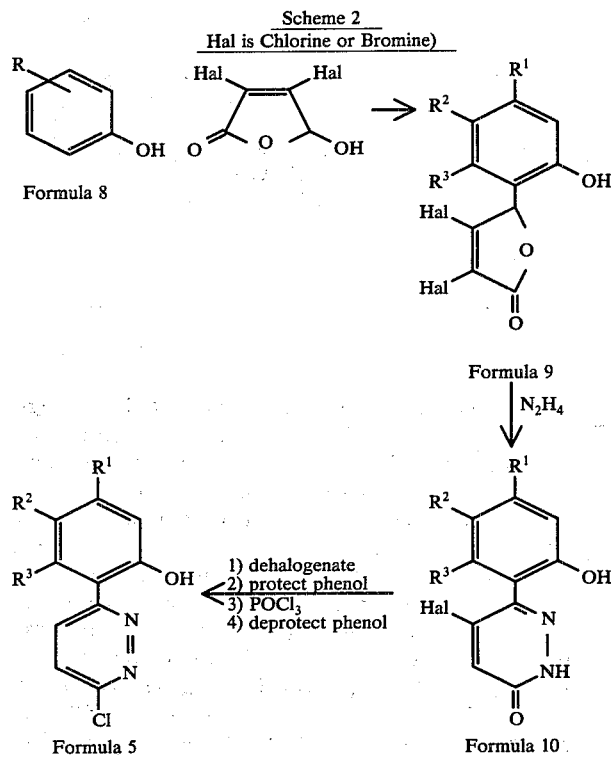

ence of a palladised charcoal catalyst or by the use of sodium 3-nitrobenzenesulphonate, protection of the phenolic hydroxy, e.g., by using ethyl chloroformate, conversion of the pyridazinone into a 3-chloropyridazine, e.g. by using phosphoryl chloride, and deprotection of the protected phenolic hydroxyl, e.g. by treatment with mild alkali in the case of the ethoxycarbonyl derivative.

The compounds of Formula 1 wherein X is OH (represented by Formula 5) may alternatively be prepared by a process set out in Scheme 3:

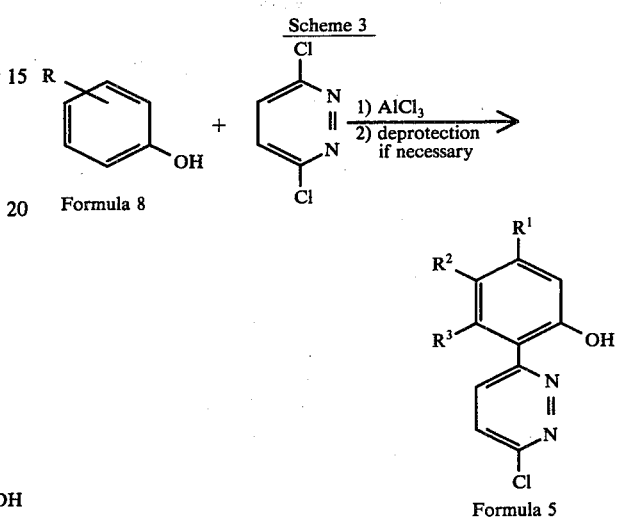

A phenol of Formula 8 (preferably a para-substituted phenol) is treated with a mucohalic acid and an appropriate catalyst (such as zinc chloride, polyphosphoric acid or aluminium trichloride) to give a γ-aryl-α,β-dihalo-Δ$^{αβ}$-crotonolactone of Formula 9 (or the corresponding 3-acyl-3-haloacrylic acid or ester). When $R^1$, $R^2$ and $R^3$ are all hydrogen it is preferred that the para postion of the phenol is blocked by a t-butyl group which may be removed at a later stage with aluminium chloride and an excess of a suitable aromatic compound such as toluene or anisole which can be easily alkylated under Friedel-Crafts conditions. The compounds of Formula 10 may be converted into the compounds of Formula 5 by a series of reactions involving dehalogenation, e.g. by the use of hydrogen in the pres- A phenol of Formula 8 is treated with a 3,6-dichloropyridazine and a suitable catalyst, e.g. aluminium trichloride, in a suitable solvent, e.g. nitrobenzene, to give a compound of Formula 5 by a Friedel-Crafts reaction. Preferably the phenol of Formula 8 is an activated phenol, such as resorcinol. When this reaction is used to prepare a compound of Formula 5 wherein $R^1$, $R^2$ and $R^3$ are all hydrogen it is preferred that the phenol of Formula 8 has a para-protecting group, such as t-butyl.

The compounds of Formula 1 wherein X is

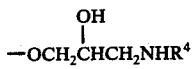

may be prepared from the compounds of Formula 1 wherein X is OH (also represented by Formula 5) by successive treatment with epichlorohydrin or epibromohydrin, and an amine $R^4NH_2$.

The compounds of Formula 1 are useful as intermediates in the production of hydrazinopyridazine compounds of Formula 11, which are described inter alia in our co-pending U.S. application Ser. No. 583,379, now U.S. Pat. No. 4,053,601 and which have β-adrenergic blocking and vasodilator activity.

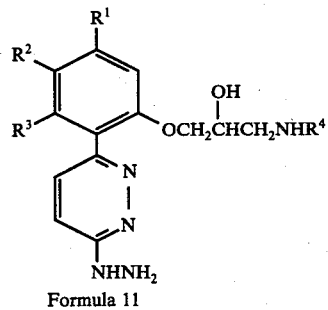

Formula 11

In Formula 11, $R^1$, $R^2$, $R^3$ and $R^4$ have the same significance as in Formula 1. Compounds of Formula 11 may be prepared by treating a compound of Formula 1 wherein X is

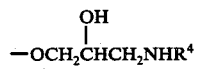

with hydrazine.

The compounds of Formula 1 wherein X is

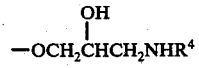

also have useful β-adrenergic blocking activity, which may be demonstrated in a suitable test preparation such as cats anaesthetised with pentobarbitone sodium 60 mg/Kg i.p. In such anaesthetised cats, intravenous injections of isoprenaline cause tachycardia, and vasodilation in the hind-lamb. These effects of isoprenaline (which are dose-dependent and are due to stimulation of β-adrenoceptors) can be reduced or abolished by intravenous administration of from 0.01 to 100 micromoles/Kg of a compound of Formula 1 wherein X is

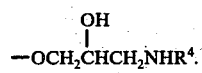

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric, acetic, citric and maleic acids.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Examplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 500 mg. If a liquid carrier is used, the preparation may be in the form of a syrup, emulsion, soft gelatin capsule, sterile injectable liquid such as in an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to produce β-adrenergic blockade. The route of administration may be oral or parenteral.

Preferably, each dosage unit will contain the active ingredient in an amount of from about 25 mg to about 500 mg most preferably from about 50 mg to about 250 mg.

The active ingredient will preferably be administered in equal doses one to three times per day. The daily dosage regimen will preferably be from about 100 mg to about 2 g.

Other pharmacologically active compounds may in certain cases be included in the composition. Advantageously the composition will be made up in a dosage unit form appropriate to the desired mode of administration for example to the desired mode of administration for example as a tablet, capsule or injectable solution.

The invention is illustrated but not limited by the following Examples wherein temperatures are given in degrees of Centigrade.

EXAMPLE 1

3-Chloro-6-[2-(3-t-butylamino-2-hydroxypropoxy)-4-methoxyphenyl]-pyridazine (i) 3-Chloro-6-(2,4-dihydroxyphenyl)pyridazine (4.0 g, 0.18 mole), dimethyl sulphate (2.55 g, 0.0201 mole), potassium carbonate (10.0 g, 0.072 mole) and dry acetone (100 ml) were stirred at room temperature for 20 hours. The reaction mixture was filtered and the inorganic residue was washed with more acetone. Evaporation of the combined filtrates gave a brown residue which was extracted with dilute sodium hydroxide solution. The aqueous extract was washed with dichloromethane, treated with charcoal, filtered and acidified. The resulting precipitate was collected, washed with water and crystallised from ethanol to give 3-chloro-6-

(2-hydroxy-4-methoxyphenyl)pyridazine (2.2 g, 49%; m.p. 156°–157°).

(ii) A stirred mixture of 3-chloro-6-(2-hydroxy-4-methoxyphenyl)pyridazine (0.1 mole), potassium carbonate (0.3 mole) and epibromohydrin (0.4 mole) in butan-2-one was heated under reflux overnight. The filtered solution was evaporated to give an oil which was purified by elution with mixtures of chloroform-methanol on a silica column to give 3-chloro-6-[2-(2,3-epoxypropoxy)-4-methoxyphenyl]pyridazine m.p. 111°–112° (ethanol).

(iii) A solution of 3-chloro-6-[2-(2,3-epoxypropoxy)-4-methoxyphenyl]pyridazine (0.05 mole) and t-butylamine (0.5 mole) in methanol was allowed to stand at room temperature for 40 hours. Evaporation of the reaction mixture gives 3-chloro-6-[2-(3-t-butylamino-2-hydroxypropoxy-4-methoxyphenyl]-pyridazine m.p. 133°–135°. The hydrochloride had m.p. 262°–265°.

(iv) A stirred mixture of hydrazine hydrate (30 ml) and 6-[2-(3-t-butylamino-2-hydroxypropoxy)-4-methoxyphenyl]-3-chloropyridazine (2.9 g) was heated under reflux for 5 hours, and was cooled to 0°. The oil which separated out was dissolved in chloroform and this solution was washed with water, and with dilute hydrochloric acid, and evaporated to give 3-[2-(3-t-butylamino-2-hydroxypropoxy)-4-methoxyphenyl]-6-hydrazinopyridazine dihydrochloride, m.p. 240°–245° (methanol)

EXAMPLE 2

3-Chloro-6-[4-allyloxy-2-(3-t-butylamino-2-hydroxypropoxy)phenyl]pyridazine (i) 3-Chloro-6-(2,4-dihydroxyphenyl)pyridazine was reacted with allyl bromide under similar conditions to those described in Example 1(i), to give 3-chloro-6-(4-allyloxy-2-hydroxyphenyl)-pyridazine.

(ii) 3-Chloro-6-(4-allyloxy-2-hydroxyphenyl)pyridazine was employed in a series of reactions similar to those described in Example 1 (ii–iii) to give the title compound, m.p. 93°–94°.

EXAMPLE 3

3-Chloro-6-[2-(3-t-butylamino-2-hydroxypropoxy)-4-hydroxyphenyl]pyridazine (i) 3-Chloro-6-(2,4-dihydroxyphenyl)pyridazine (1 mole) was treated with ethyl chloroformate (1.1 mole) in pyridine to give 3-chloro-6-(4-ethoxycarbonyloxy-2-hydroxyphenyl)pyridazine.

(ii) 3-Chloro-6-(4-ethoxycarbonyloxy-2-hydroxyphenyl)pyridazine was employed in a series of reactions similar to those described in Example 1 (ii–iii) and the product dissolved in dilute sodium hydroxide solution and the solution treated with acid to give the title compound.

EXAMPLE 4

3-Chloro-6-[2-(3-t-butylamino-2-hydroxypropoxy)-phenyl]pyridazine (i) Hydrazine hydrate (1.2 ml) was added to a stirred suspension of 3-(2-hydroxybenzoyl)propionic acid (3.1 g) in water (20 ml), and the mixture was heated under reflux for ¾ hour. The mixture was diluted with an equal volume of water, allowed to cool, and filtered to give 6-(2-hydroxyphenyl)-4,5-dihydro-3(2H)pyridazinone (2.6 g) m.p. 211°–212°.

(ii) Sodium 3-nitrobenzenesulphonate (2.96 g) and 6-(2-hydroxyphenyl)-4,5-dihydro-3(2H)pyridazinone (2.5 g) were added to a stirred solution of sodium hydroxide (1.31 g) in water (25 ml) and the mixture was heated under reflux for 2.5 hours. Acetic acid was added to the warm stirred solution until there was no further precipitation and the mixture was pH 9. The mixture was filtered to give 6-(2-hydroxyphenyl)-3(2H)-pyridazinone (2.05 g) m.p. 287°–292°. A sample recrystallised from 2-methoxyethanol had m.p. 295°–299°.

(iii) A mixture of 6-(2-hydroxyphenyl)-3(2H)-pyridazinone (20 g), acetic anhydride (60 ml) and pyridine (10 drops) was heated and stirred on a steam-bath for 1¾ hours. The mixture was evaporated under reduced pressure, and the residual oil was treated with water (100 ml) and methanol (10 ml) and was allowed to crystallise to give 6-(2-acetoxyphenyl)-3(2H)-pyridazinone (22.7 g) m.p. 181°–183.5°. A sample recrystallised from 50% aqueous ethanol had m.p. 182.5°–184.5°.

(iv) A mixture of 6-(2-acetoxyphenyl)-3(2H)pyridazinone (22.4g) and phosphoryl chloride (90 ml) was stirred and warmed at 55°–60° for 40 minutes. The phosphoryl chloride was removed under reduced pressure at 50° and the residual oil was poured on to ice (200 g). The mixture was allowed to stand overnight at 5° and was filtered to give 3-chloro-6-(2-acetoxyphenyl)-pyridazine (23.1 g m.p. 131°–133.5°. A sample recrystallised from ethanol had m.p. 137°–138°.

(v) A mixture of 3-chloro-6-(2-acetoxyphenyl)pyridazine (23.1 g), aqueous sodium hydroxide (2N, 56 ml) and ethanol (10 ml) was stirred at room temperature for 1 hour. The mixture was diluted with an equal volume of water, adjusted to pH 2 with concentrated hydrochloric acid and was filtered to give 3-chloro-6-(2-hydroxyphenyl)pyridazine (18.7 g) m.p. 187.5°–188.5°. A sample recrystallised from ethanol had m.p. 187.5°–188.5°.

(vi) A mixture of 3-chloro-6-(2-hydroxphenyl)pyridazine (2.69 g), epibromohydrin (4.5 ml), anhydrous potassium carbonate (3.6 g) and dry butan-2-one (100 ml) was stirred and heated under reflux for 16 hours. The mixture was filtered and the filtrate was evaporated to dryness and the residue was twice recrystallised from ethanol to give 3-chloro-6-(2-epoxypropoxyphenyl)-pyridazine (1.49 g) m.p. 118°–119°.

(vii) A mixture of 3-chloro-6-(2-epoxypropoxyphenyl)pyridazine (0.7 g), methanol (7 ml) and t-butylamine (1.7 ml) was stirred and heated under reflux for 1¼ hours. The mixture was evaporated under reduced pressure at 50° and the residue was recrystallised from toluene to give the title product (1.28 g) m.p. 136.5°–137.5°.

This product was treated with hydrochloric acid (1.0N, 3.62 ml), the solution was extracted with dichloromethane and the aqueous solution was evaporated under reduced pressure and the residue was recrystallised from ethanol/ether to give 3-chloro-6-[2-(3-t-butylamino-2-hydroxpropoxy)phenyl]pyridazine hydrochloride (1.2 g) m.p. 193.5°–194.5°.

(viii) A stirred mixture of 3-chloro-6-[2-(3-t-butylamino-2-hydroxypropoxy)phenyl]pyridazine hydrochloride (0.3 g) and hydrazine hydrate (3 ml) was heated under reflux for 50 minutes. After cooling, dichloromethane was added and this mixture was extracted with water, the dichloromethane was removed by evaporation and the residue was treated with a mixture of n-propanol (1.2 ml) and concentrated hydrochloric acid (0.13 ml) to give 3-[2-(3-t-butylamino-2-hydroxypropoxy)phenyl]-6-hydroazinopyridazine dihydrochloride, m.p. 163°–168°

Substitution of
(a) 3-(4-fluoro-2-hydroxypbenzoyl)propionic acid and
(b) 3-(5-bromo-2-hydroxybenzoyl)propionic acid for 3-(2-hydroxybenzoyl)propionic acid in the above procedure gave:

(i)

(a) 6-(4-fluoro-2-hydroxyphenyl)4,5-dihydro-3(2H)pyridazinone m.p. 252°–243°
(b) 6-(5-bromo-2-hydroxyphenyl)4,5-dihydro-3(2H)pyridazinone m.p. 268°–270°

(ii)

(a) 6-(4-fluoro-2-hydroxyphenyl)-3(2H)pyridazinone, m.p. above 270° (decomp.)
(b) 6-(5-bromo-2-hydroxyphenyl)-3(2H)pyridazinone, m.p. above 270° (decomp.)

(iii)

(a) 6-(2-acetoxy-4-fluorophenyl)-3(2H)pyridazinone, m.p. 170°–171°
(b) 6-(2-acetoxy-5-bromophenyl)-3(2H)pyridazinone (v)

(a) 3-chloro-6-(4-fluoro-2-hydroxyphenyl)pyridazine m.p. 187°–188°
(b) 3-chloro-6-(5-bromo-2-hydroxyphenyl)pyridazine m.p. 183°–184°

(vi)

(a) 3-chloro-6-(4-fluoro-2-epoxypropoxyphenyl)-pyridazine, m.p. 102°–103°
(b) 3-chloro-6-(5-bromo-2-epoxypropoxyphenyl)-pyridazine, m.p. 141°–142°

(vii)

(a) 3-chloro-6-[2-(3-t-butylamino-2-hydroxypropoxy)-4-fluorophenyl]pyridazine, m.p. 110°–112°
(b) 3-chloro-6-[5-bromo-2-(3-t-butylamino-2-hydroxypropoxy)phenyl]pyridazine, m.p. 93°–94°

Substitution of 3-(4-chloro-2-hydroxybenzoyl)propionic acid for 3-(2-hydroxybenzoyl)propionic acid in the above procedure gives 3-chloro-6-[2-(3-t-butylamino-2-hydroxypropoxy)-4-chlorophenyl]pyridazine

EXAMPLE 5

3-Chloro-6-[2-(3-isopropylamino-2-hydroxypropoxy)-4-methoxyphenyl]pyridazine

Substitution of isopropylamine for t-butylamine in the procedure of Example 1(iii) gave the title compound m.p. 128°–129°.

EXAMPLE 6

3-Chloro-6-[2-(3-t-butylamino-2-hydroxypropoxy)-4-ethoxyphenyl]pyridazine

Substitution of diethyl sulphate for dimethyl sulphate in the general procedure of Example 1 gave the title compound m.p. 115°–117° via 3-chloro-6-[2-(2,3-epoxypropoxy)-4-ethoxyphenyl]pyridazine m.p. 93°–94°.

EXAMPLE 7

3-Chloro-6-[2-(3-(2-phenylethyl)-2-hydroxypropoxy)-4-methoxyphenyl]pyridazine

Substitution of a 2-phenylethylamine for t-butylamine in the procedure of Example 1(iii) gives the title compound.

EXAMPLE 8

| Ingredients | Amounts |
|---|---|
| 3-Chloro-6-(2-(3-t-butylamino-2-hydroxypropoxy)phenyl)pyridazine | 75 mg |
| Sucrose | 40 mg |
| Starch | 15 mg |
| Talc | 3 mg |
| Stearic Acid | 1 mg |

The ingredients are screened, mixed and filled into a hard gelatin capsule.

EXAMPLE 9

| Ingredients | Amounts |
|---|---|
| 3-Choro-6-(2-(3-t-butylamino-2-hydroxypropoxy)phenyl)pyridazine | 100 mg |
| Lactose | 50 mg |

The ingredients are screened, mixed and filled into a hard gelatin capsule.

We claim:

1. A compound of the formula:

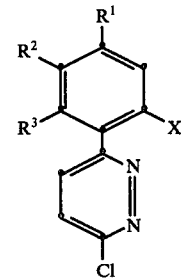

wherein two of the groups $R^1$, $R^2$ and $R^3$ are hydrogen and the third group is hydrogen, fluoro, chloro, bromo, hydroxy, lower alkoxy, lower alkenyloxy or lower alkoxycarbonyl; and X is

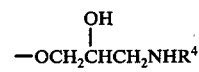

where $R^4$ is isopropyl, tertiary butyl or 2-phenylethyl, or when $R^1$, $R^2$ and $R^3$ are other than hydroxy, X may also be hydroxy.

2. A compound of claim 1 wherein $R^1$, $R^2$ and $R^3$ are all hydrogen, or one of $R^1$, $R^2$ and $R^3$ is fluoro, chloro or methoxy.

3. A compound of claim 1 wherein $R^3$ is hydrogen.

4. A compound of claim 1 wherein X is

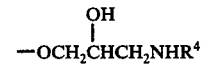

and $R^4$ is isopropyl or tertiary butyl.

5. A compound of claim 1 wherein $R'$, $R^2$, $R^3$ are hydrogen and $R^4$ is isopropyl or tertiary butyl.

6. A compound of claim 1, said compound being 3-chloro-6-(2-hydroxyphenyl)pyridazine.

7. A compound of claim 1, said compound being 3-chloro-6-[2-(3-t-butylamino-2-hydroxypropoxy)-phenyl]pyridazine.

8. A compound of claim 1, said compound being 3-chloro-6-[2-(2-hydroxy-3-isopropylaminopropoxy)-phenyl]pyridazine.

9. A compound of claim 1, said compound being 3-chloro-6-(2-hydroxy-4-methoxyphenyl)pyridazine.

10. A compound of claim 1, said compound being 3-chloro-6-[2-(3-t-butylamino-2-hydroxypropoxy)-4-methoxyphenyl]pyridazine.

11. A compound of claim 4 in the S-absolute configuration.

* * * * *